US006752785B2

(12) United States Patent
Van Antwerp et al.

(10) Patent No.: US 6,752,785 B2
(45) Date of Patent: Jun. 22, 2004

(54) LEAK DETECTION SYSTEM AND METHOD OF USING THE SAME

(75) Inventors: William P. Van Antwerp, Valencia, CA (US); Sheldon B. Moberg, Granada Hills, CA (US); Cary D. Talbot, Santa Clarita, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 169 days.

(21) Appl. No.: 10/190,168

(22) Filed: Jul. 3, 2002

(65) Prior Publication Data

US 2003/0009131 A1 Jan. 9, 2003

Related U.S. Application Data

(63) Continuation-in-part of application No. 09/524,021, filed on Mar. 13, 2000, now Pat. No. 6,461,329.

(51) Int. Cl.[7] .............................................. A61M 5/00
(52) U.S. Cl. ..................... 604/111; 604/151; 604/180
(58) Field of Search ................................ 604/111, 151, 604/180, 174; 340/605

(56) References Cited

U.S. PATENT DOCUMENTS

| | | | | |
|---|---|---|---|---|
| 3,399,971 | A | | 9/1968 | Kita ............................. 23/230 |
| 4,122,838 | A | | 10/1978 | Leonard ..................... 128/2 S |
| 4,239,495 | A | | 12/1980 | Gindler et al. ............. 23/230 B |
| 4,350,155 | A | | 9/1982 | Thompson .............. 128/213 R |
| 4,378,808 | A | | 4/1983 | Lichtenstein ................ 128/736 |
| 4,602,249 | A | * | 7/1986 | Abbott ........................ 340/605 |
| 4,619,653 | A | | 10/1986 | Fischell ....................... 604/891 |
| 4,699,615 | A | | 10/1987 | Fischell et al. .............. 604/131 |
| 4,717,378 | A | | 1/1988 | Perrault et al. ................ 604/20 |
| 4,731,051 | A | | 3/1988 | Fischell ........................ 604/67 |
| 4,784,645 | A | | 11/1988 | Fischell ....................... 604/153 |
| 4,787,398 | A | | 11/1988 | Garcia et al. ................ 128/770 |
| 5,153,827 | A | | 10/1992 | Coutrë et al. ........... 364/413.02 |
| 5,399,445 | A | | 3/1995 | Tinker .......................... 429/90 |
| 5,468,621 | A | | 11/1995 | Kojima et al. ................. 435/25 |
| 5,557,263 | A | | 9/1996 | Fisher et al. ................. 340/605 |
| 5,790,036 | A | | 8/1998 | Fisher et al. ................. 340/605 |
| 6,057,689 | A | | 5/2000 | Saadat ......................... 324/557 |
| 6,689,100 | B2 | * | 2/2004 | Connelly et al. ............. 604/117 |

FOREIGN PATENT DOCUMENTS

| | | | |
|---|---|---|---|
| GB | 227906 | 1/1925 | |
| WO | 0113785 | 3/2001 | ............ A61B/5/00 |

* cited by examiner

*Primary Examiner*—John Rivell
(74) *Attorney, Agent, or Firm*—Medtronic MiniMed, Inc.

(57) ABSTRACT

In a fluid delivery system for delivering a fluid into an individual's body, a leak detection system indicates that the fluid has leaked outside a normal fluid path of the fluid delivery system, such as near an infusion site or a fluid-filled reservoir. Preferably, the leak detection system includes a chemical positioned near the infusion site that reacts with preservatives in the leaking fluid to generate a highly visible, brightly colored, chemical complex. Alternatively, mechanical, electro-optical, electrochemical, electrical or other chemical systems may be used to detect the presence of fluid that is leaking near the infusion site. Further, the leak detection systems may be used to detect the presence of fluid that is leaking from or near other locations within the fluid delivery system, such as on or near a fluid-filled reservoir, or a flexible tube coupled between the reservoir and the infusion site.

42 Claims, 7 Drawing Sheets

LEAK DETECTION SYSTEM AND METHOD OF USING THE SAME

RELATED APPLICATIONS

This application is a continuation-in-part of U.S. patent application Ser. No. 09/524,021, filed on Mar. 13, 2000, and entitled "Infusion Site Leak Detection System and Method of Using the Same" now U.S. Pat. No. 6,461,329.

FIELD OF THE INVENTION

This invention relates to leak detection systems, and in particular embodiments, to leak detection systems that detect when fluid is leaking outside a normal fluid path of a fluid delivery system for delivering the fluid into an individual's body, such as near an infusion site or a fluid containing element.

BACKGROUND OF THE INVENTION

Continuous subcutaneous infusion of medications is becoming increasingly important. Typically, an individual uses a small pager-size programmable pump to deliver a medication through a flexible plastic tube to an infusion set. The infusion set delivers medication to an individual's subcutaneous tissue through the use of either a rigid needle that is left in the tissue or through a flexible cannula that remains in the tissue after being inserted via a removable needle. The most common infused fluid is insulin. Currently, more than 70,000 individuals in the United States, and about 30,000 more individuals worldwide, use subcutaneous infusion of insulin for the treatment of diabetes mellitus. However, other infused fluids include HIV drugs, drugs to treat pulmonary hypertension, iron chelation drugs, pain medications, and anti-cancer treatments.

Generally, one end of the cannula is attached to the infusion set and the other end is inserted through the individual's skin. An adhesive pad on a bottom of the infusion set adheres the infusion set to the individual's skin. Clear adhesive tape is often placed over the infusion set and in contact with the individual's skin to further secure the infusion set and cannula.

A leak near the infusion site can be one of the most serious problems that occurs while infusing a medication. Traditionally, leaks near the infusion site are caused by inadvertently pulling the cannula out of the body, or separating the cannula from an infusion set, or an inadequately sealed infusion set. A medication leaking near the insertion site is often trapped by the adhesive and collects between the infusion set and the skin. Even though the infusion set is typically made of clear plastic, it is hard for the individual to look at the infusion set and tell the difference between medication passing through the infusion set, and medication collecting under the infusion set. A leak from or near a reservoir or a plastic tube filled with the medication can also be a common problem that occurs while infusing the medication. The medication often leaks at interfaces within the infusion system, such as at a connector between a fluid-filled reservoir and a tube coupled to the infusion set.

Further, most infused medications are delivered at a rate as low as a few micro liters per hour ($\mu$l/Hr.). This delivery rate is so slow that individuals typically cannot discern between body moisture, such as sweat, and medication that has leaked onto the surface of their skin, such as near the infusion site. Thus, hours may pass before a medication begins to seep out from under the adhesive pad and drip down the individual's skin, drawing their attention to the leak. In the meantime, the individual may suffer significant consequences due to the lack of medication in their system. In the case of a diabetic individual infusing insulin, for example, the user could pass out due to hyperglycemia before realizing that insulin is not entering their body.

SUMMARY OF THE DISCLOSURE

According to an embodiment of the invention, a leak detection system is to detect the presence of a fluid to be delivered into an individual's body that has leaked near an infusion site. Embodiments of the present invention include a delivery device, a delivery element, and at least one chemical. The delivery device is adapted for attachment to the individual's body. The delivery element is configured to penetrate the individual's body at the infusion site and establish fluid communication between the delivery device and the individual's body, so that the fluid can travel from the delivery device into the individual's body. The at least one chemical is positioned near the infusion site and reacts with at least one component within the fluid when the fluid is present near the infusion site.

In particular embodiments, a product of a chemical reaction, between the at least one chemical positioned near the infusion site and the at least one component within the fluid, is a colored complex. In specific embodiments, the at least one chemical positioned near the infusion site contains at least 4-amino-antipyrine and potassium ferricyanide. In other embodiments, the at least one chemical positioned near the infusion site contains at least 4-amino-antipyrine and potassium ferricyanide and horse radish peroxidase (HRP). Alternatively, the at least one chemical positioned near the infusion site contains at least ninhydrin. In additional embodiments, the at least one chemical positioned near the infusion site contains at least Coomassie Brilliant Blue.

Various methods may be used to position the at least one chemical near the infusion site. In some embodiments, the at least one chemical positioned near the infusion site is encapsulated in micro-spheres. In other embodiments, the at least one chemical positioned near the infusion site is a component of a gel. In further embodiments, the at least one chemical positioned near the infusion site is a component of an adhesive. And in still further embodiments, the at least one chemical positioned near the infusion site is associated with starch granules. In particular embodiments, the delivery device includes a base, and the at least one chemical positioned near the infusion site is embedded in the base of the delivery device. Finally, in other embodiments, the at least one chemical positioned near the infusion site is deposited on the individual's body.

According to another embodiment of the invention, a leak detection system to detect the presence of a fluid to be delivered into an individual's body that has leaked near an infusion site includes a delivery device, a delivery element, an adhesive tape, and at least one chemical. The delivery device is adapted for attachment to the individual's body. The delivery element is configured to penetrate the individual's body at the infusion site and establish fluid communication between the delivery device and the individual's body, so that the fluid can travel from the delivery device into the individual's body. The adhesive tape is applied to a portion of the individual's body to hold the delivery device on the individual's body. The at least one chemical is associated with the adhesive tape and reacts with at least one component within the fluid when the fluid is present near the infusion site.

In particular embodiments, a product of a chemical reaction between the at least one chemical associated with the adhesive tape, and the at least one component within the fluid, is a colored complex. In additional embodiments, the at least one chemical associated with the adhesive tape is included with the adhesive on the adhesive tape.

According to a further embodiment of the invention, the leak detection system, to detect the presence of a fluid to be delivered into an individual's body that has leaked near an infusion site, includes a delivery device, a delivery element, at least one chemical, an optical receiver, and a light conducting element. The delivery device is adapted for attachment to the individual's body. The delivery element is configured to penetrate the individual's body at the infusion site and establish fluid communication between the delivery device and the individual's body, so that the fluid can travel from the delivery device into the individual's body. The at least one chemical is positioned near the infusion site, and reacts with at least one component within the fluid when the fluid is present near the infusion site. A product of a chemical reaction between the at least one chemical positioned near the infusion site and the at least one component within the fluid is a colored complex. The light conducting element guides light from a point near the infusion site to the optical receiver. The optical receiver detects a change in light when the colored complex is created by the chemical reaction and provides an output signal indicating that a leak is detected. In particular embodiments, the light conducting element is at least one fiber optic cable. In alternative embodiments, the light conducting element is a flexible plastic tube filled with the fluid. In particular embodiments, the leak detection system includes an alarm system, controlled by the output signal, to notify the individual when a leak is detected. In more particular embodiments, the alarm system produces an audible sound when a leak is detected, and in other embodiments, the alarm system activates a vibrator when a leak is detected.

According to yet another embodiment of the invention, a leak detection system to detect the presence of a fluid to be delivered into an individual's body that has leaked near an infusion site includes a delivery device, a delivery element, a rosette, at least one electrical component, and a battery. The delivery device is adapted for attachment to the individual's body, and the delivery device includes a delivery device base. The delivery element is configured to penetrate the individual's body at the infusion site and establish fluid communication between the delivery device and an individual's body, so that the fluid can travel from the delivery device into the individual's body. The rosette is positioned on the delivery device base and substantially surrounds the delivery element. The at least one electrical component is coupled to the rosette and detects a change in at least one electrical characteristic associated with the rosette when a leak occurs. The battery supplies power to the at least one electrical component.

In particular embodiments, the rosette is a closed circuit, and the impedance across the rosette decreases as fluid leaks near the infusion site. In alternative embodiments, the rosette is a closed circuit before a leak occurs, and at least portions of the rosette dissolve in the presence of the fluid. The impedance across the rosette increases as the at least portions of the rosette dissolve. In other particular embodiments, the rosette is an open circuit, and the circuit is closed when fluid leaks near the infusion site. In alternative particular embodiments, one or more chemicals are positioned near the infusion site, and leaking fluid near the infusion site triggers an electrochemical reaction with the chemicals.

In particular embodiments, the at least one electrical component measures voltage across the rosette. In other particular embodiments, the at least one electrical component measures impedance across the rosette. In still other embodiments, the at least one electrical component measures capacitance across the rosette.

In other embodiments, the leak detection system includes an alarm system, coupled to the battery and to the at least one electrical component, to notify and indicate when a leak is detected. The alarm system produces an audible sound when a leak is detected. In alternative embodiments, the alarm system activates a vibrator when a leak is detected.

According to an embodiment of the invention, a leak detection system to detect the presence of a fluid to be delivered into an individual's body that has leaked near an intended delivery site includes a delivery attachment element, a delivery element, and at least one reactive element. The delivery attachment element is adapted for attachment to the delivery site and the delivery element. The delivery element is configured to penetrate the delivery site and establish fluid communication between the delivery attachment element and the individual's body, so that the fluid can travel from the delivery attachment element and into the individual's body. The at least one reactive element is positioned near the delivery site and coupled to at least one of, the delivery attachment element and the delivery element, so that when the fluid is present near the delivery site, the at least one reactive element reacts with at least one component within the fluid.

According to another embodiment of the invention, a leak detection system to detect the presence of a fluid that has leaked outside a normal fluid path of a fluid delivery system for delivering the fluid into an individual's body includes a fluid containing element, a delivery element, and at least one chemical. The fluid containing element is adapted to be filled with the fluid to be delivered into the individual's body and placed in a device for delivering the fluid into the individual's body. The delivery element is configured to penetrate the individual's body and establish fluid communication between the fluid containing element and the individual's body so that the fluid can travel along the normal fluid path from the fluid containing element through the delivery element into the individual's body. The at least one chemical is positioned near the fluid containing element and reacts with at least one component within the fluid when the fluid is present near an exterior surface of the fluid containing element.

In particular embodiments, the fluid containing element is a reservoir. In other embodiments, the fluid containing element is a tube coupled between the delivery element and the device for delivering the fluid into the individual's body. In still other embodiments, the at least one chemical positioned near the fluid containing element is deposited on the exterior surface of the fluid containing element. Alternatively, the at least one chemical positioned near the fluid containing element is associated with a label applied onto the exterior surface of the fluid containing element. In yet other embodiments, the at least one chemical positioned near the fluid containing element is deposited on a portion of the device for delivering the fluid into the individual's body. Alternatively, the at least one chemical positioned near the fluid containing element is associated with a label applied onto a portion of the device for delivering the fluid into the individual's body.

According to a further embodiment of the invention, a leak detection system to detect the presence of the fluid that has leaked outside a normal fluid path of a fluid delivery system for delivering a fluid into an individual's body includes a fluid containing element, a delivery element, at least one chemical, an optical receiver, and a light conducting element. The fluid containing element is adapted to be filled with the fluid to be delivered into the individual's body and placed in a device for delivering the fluid into the individual's body. The delivery element is configured to penetrate the individual's body and establish fluid communication between the fluid containing element and the individual's body so that the fluid can travel along the normal fluid path from the fluid containing element through the delivery element into the individual's body. The at least one chemical is positioned near the fluid containing element and reacts with at least one component within the fluid when the fluid is present near an exterior surface of the fluid containing element. A product of a chemical reaction between the at least one chemical positioned near the fluid containing element and the at least one component within the fluid is a colored complex. A light conducting element guides light from a point near the fluid containing element to the optical receiver. The optical receiver detects a change in light when the colored complex is created by the chemical reaction and provides an output signal indicating that a leak is detected.

According to yet another embodiment of the invention, a leak detection system to detect the presence of the fluid that has leaked outside a normal fluid path of a fluid delivery system for delivering a fluid into an individual's body includes a fluid containing element, a delivery element, a rosette, at least one electrical component, and a battery. The fluid containing element is adapted to be filled with the fluid to be delivered into the individual's body and placed in a device for delivering the fluid into the individual's body. The delivery element is configured to penetrate the individual's body and establish fluid communication between the fluid containing element and the individual's body so that the fluid can travel along the normal fluid path from the fluid containing element through the delivery element into the individual's body. The rosette is positioned near the fluid containing element. The at least one electrical component is coupled to the rosette to detect a change in at least one electrical characteristic associated with the rosette when a leak occurs. The battery supplies power to the at least one electrical component.

According to a still further embodiment of the invention, a leak detection system to detect the presence of the fluid that has leaked outside a normal fluid path of a fluid delivery system for delivering a fluid into an individual's body includes a device for delivering the fluid into the individual's body, a fluid containing element, a delivery element, at least one chemical, and at least one reactive element. The fluid containing element is adapted to be filled with the fluid to be delivered into the individual's body and placed in a device for delivering the fluid into the individual's body. The delivery element is configured to penetrate the individual's body and establish fluid communication between the fluid containing element and the individual's body so that the fluid can travel along the normal fluid path from the fluid containing element through the delivery element into the individual's body. The at least one chemical is positioned near the fluid containing element and reacts with at least one component within the fluid when the fluid is present near an exterior surface of the fluid containing element. The at least one reactive element is positioned near the fluid containing element and coupled to at least one of the delivery device and the fluid containing element so that when the fluid is present near an exterior surface of the fluid containing element, the at least one reactive element reacts with at least one component within the fluid.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
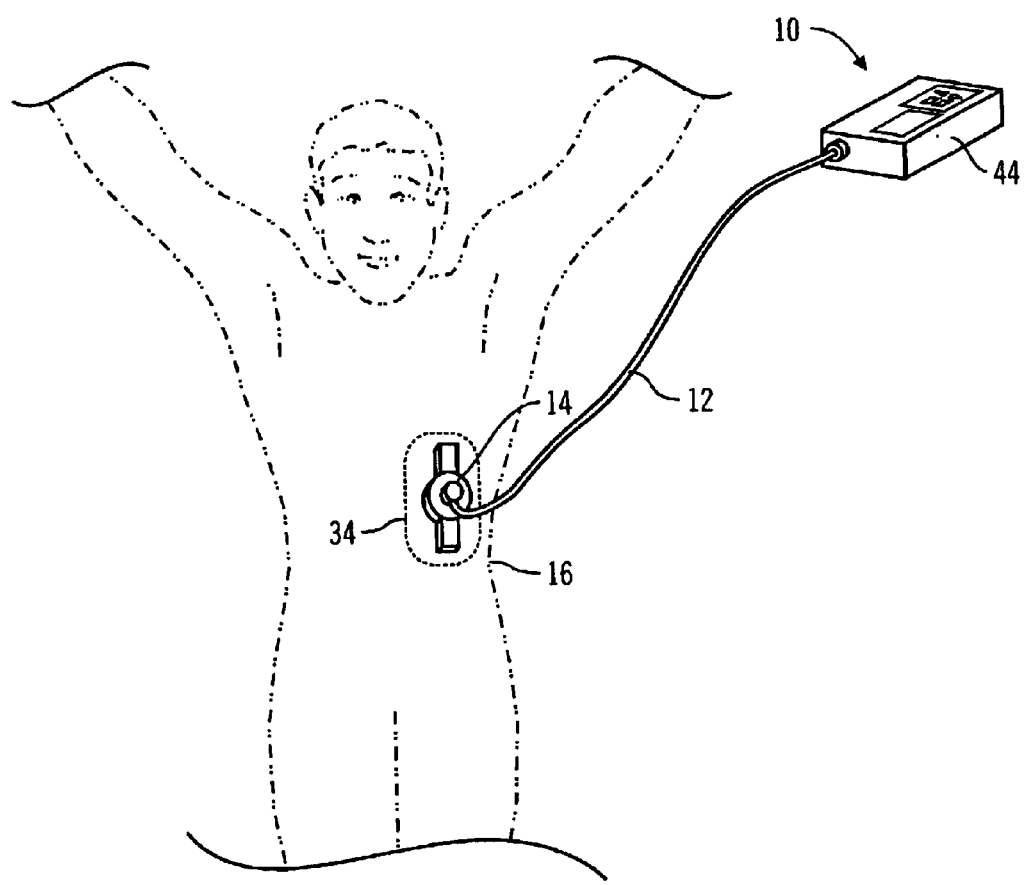
FIG. 1 is a diagram showing an infusion set attached to a body, a flexible tube, and an infusion pump according to an embodiment of the present invention.

As shown in the drawings for purposes of illustration, the invention is embodied in a leak detection system designed to indicate the presence of a fluid that leaked outside a normal fluid path of a fluid delivery system for delivering the fluid into an individual's body, such as near an infusion site, a fluid-filled reservoir, or the like. The infusion site is at a location where a delivery element, such as a cannula, needle, or the like, penetrates an individual's body. Preferably, one end of the delivery element is attached to a delivery device, and the other end is inserted through an individual's skin terminating in the individual's subcutaneous tissue. The delivery element establishes fluid communication between the delivery device and the individual's subcutaneous tissue. In alternative embodiments, the delivery element may terminate in another tissue, such as muscle, organ, inter-peritoneal, intra-peritoneal, or the like. The delivery device is attached or adjacent to the surface of the individual's skin. In preferred embodiments of the present invention, the detection system includes a chemical positioned near the infusion site that reacts with preservatives in the leaking fluid to generate a highly visible, brightly colored, chemical complex. In alternative embodiments, mechanical, electro-optical, electrochemical, electrical or other chemical systems may be used to detect the presence of fluid that is leaking near the infusion site. In further alternative embodiments, the leak detection system may be used to detect the presence of fluid that is leaking from or near fluid containing elements within the fluid delivery system, such as on or near a fluid-filled reservoir, a tube coupled between the reservoir and the delivery element, or the like. Preferred embodiments are for use with human beings; however, alternative embodiments may be used with animals or fluid flow applications where detection of small amounts of leaking fluid is important.

An infusion pump regulates the flow of fluid into an individual's subcutaneous tissue. In preferred embodiments, shown in FIG. 1, the fluid flows along a normal fluid path from an infusion pump 10, through a flexible tube 12, and into the delivery device, such as an infusion set 14 or the like, that is adhered to the individual's skin 16. Infusion sets 14 that may be used as a delivery device are described in, but not limited to, U.S. Pat. Nos. 4,723,947; 4,755,173; 5,176,662; 5,584,813; and 6,056,718, which are herein incorporated by reference. The infusion pump 10 may be of the type described in U.S. Pat. Nos. 4,562,751; 4,685,903; 5,080,653; 5,097,122; 5,505,709; and 6,248,093; and disclosed in U.S. patent application Ser. No. 09/334,858, filed Jun. 17, 1999 and entitled "Infusion Pump With Remote Programming and Carbohydrate Calculator Capabilities," which are herein incorporated by reference. Alternatively, other infusion pumps 10 may be used for delivery of fluid through an infusion set 14 into an individual's body. In further alternative embodiments, devices other than infusion pumps 10 may be used for delivery of fluid into an individual's body, such as pen injectors (not shown) or the like.

In preferred embodiments, the infusion pump 10 comprises a relatively compact, portable housing 44 adapted to receive a fluid-filled reservoir (not shown). The infusion pump 10 includes means for operating the reservoir to deliver the fluid through the flexible tube 12 or the like into an individual's body. The infusion pump 10 and the reservoir include matingly interfitting components to ensure that the pump 10 and the reservoir are compatibly designed, and further to ensure that the reservoir is fully and properly installed within the pump 10.

Figure 11:
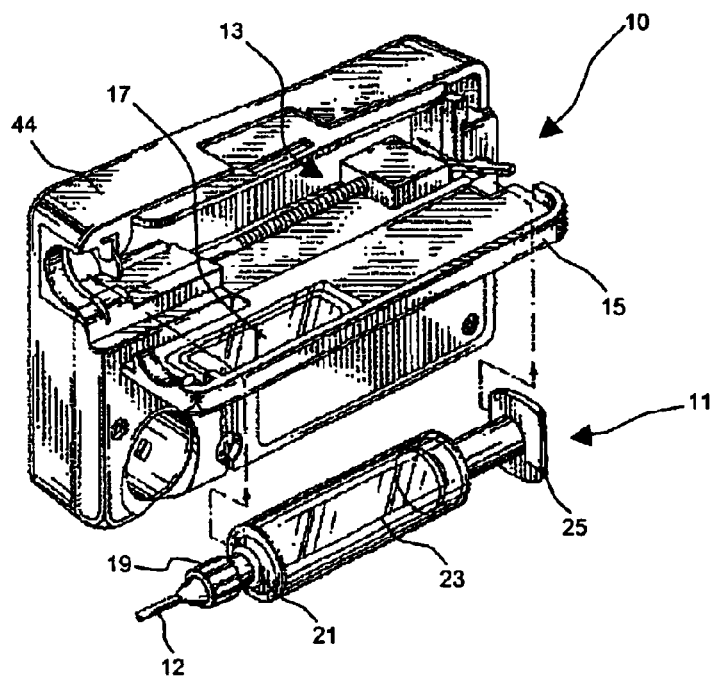
FIG. 11 is a rear perspective view of an infusion pump according to an embodiment of the present invention.

In the embodiment illustrated in FIG. 11, the infusion pump 10 comprises a relatively compact pump housing 44 defining an elongated reservoir compartment 13 adapted to receive a reservoir 11 filled with a selected fluid, such as medication to be administered to an individual. The reservoir 11 is preferably a fillable reservoir, cartridge, or syringe that is filled by the user. In alternative embodiments, the reservoir 11 may be a pre-filled reservoir, cartridge, or syringe that is pre-filled with the selected fluid. The reservoir 11 includes a barrel 23 for containing the fluid, a plunger 25 for advancing into the barrel 23 to deliver the fluid from the reservoir 11, and a luer neck 21 adapted for connection to a luer connector 19, which serves as the interface between the reservoir 11 and the tube 12. Preferably, the fluid flows along a normal fluid path from the reservoir 11 seated within the infusion pump 10, through the connector 19 and the tube 12, and into a delivery device (not shown), such as an infusion set or the like, that is adhered to the individual's skin. The pump housing 44 also includes a hinged access door 15, which is shown in an open position in FIG. 11, to permit placement of the reservoir 11 into the reservoir compartment 13, after which the door 15 can be pivoted to a closed position (not shown) during normal operation of the infusion pump 10. The pump housing 44 further includes a window 17 for viewing the reservoir 11 seated in the reservoir compartment 13 while the door 15 is in the closed position.

Figure 12:
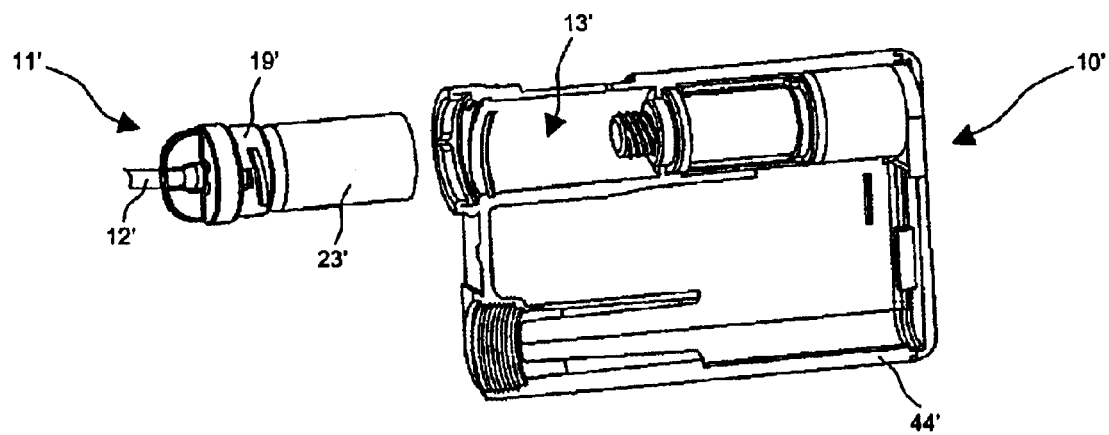
FIG. 12 is a cut-away perspective view of an infusion pump according to another embodiment of the present invention.

FIG. 12 shows another embodiment of an infusion pump 10', which is similar to the infusion pump 10 illustrated in FIG. 11. The infusion pump 10' comprises a relatively compact housing 44' defining a reservoir compartment 13' adapted to receive a reservoir 11' filled with a selected fluid. The reservoir 11' is preferably a pre-filled reservoir, cartridge, or syringe that is pre-filled with the selected fluid, such as medication. In alternative embodiments, the reservoir 11' may be a fillable reservoir, cartridge, or syringe that is filled by the user. The reservoir 11' includes a barrel 23' for containing the fluid and a plunger (not shown) for advancing into the barrel 23' to deliver the fluid from the reservoir 11'. The reservoir 11' may be filled using a handle (not shown) that is coupled to the plunger, and after being filled, the handle may be removed so that the reservoir 11' may be placed in the infusion pump 10'. The reservoir 11' further includes a connector 19', which serves as the interface between the reservoir 11 and the tube 12', and may be of the type disclosed in U.S. patent application Ser. No. 09/428,818, filed Oct. 28, 1999 and entitled "Reservoir Connector", which is herein incorporated by reference. Preferably, the fluid flows along a normal fluid path from the reservoir 11' seated within the infusion pump 10', through the connector 19' and the tube 12', and into a delivery device (not shown), such as an infusion set or the like, that is adhered to the individual's skin. The pump housing 44' may also include a window (not shown) for viewing the reservoir 11' while seated in the reservoir compartment 13'.

Figure 2A:
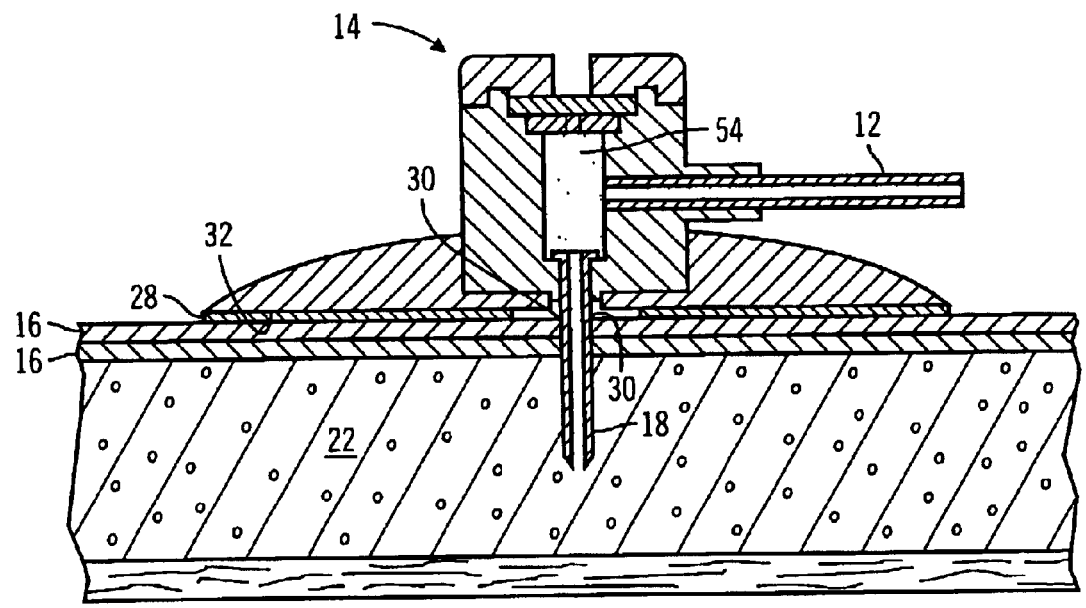
FIG. 2a is a cross-sectional side view of an infusion set attached to a body tissue.
Figure 3A:
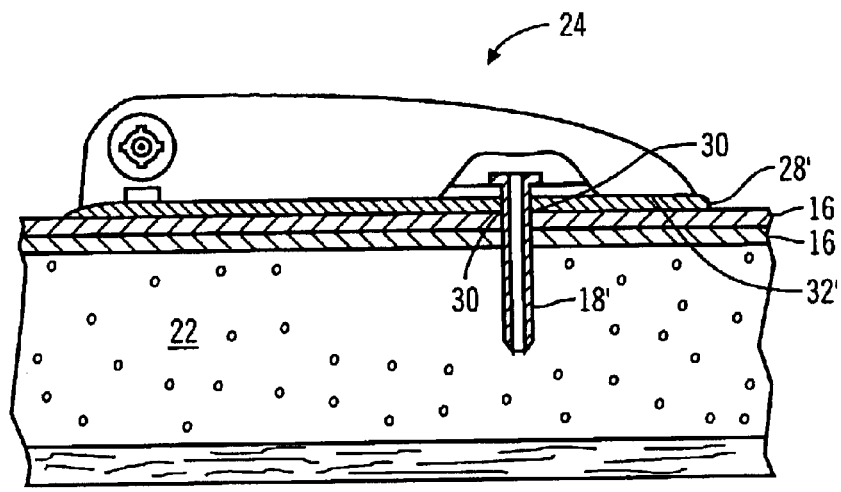
FIG. 3a is a side view of an infusion pump attached to a body tissue, with a partial cut away of the pump, showing a cross-sectional view of a delivery element penetrating the body tissue.
Figure 3B:
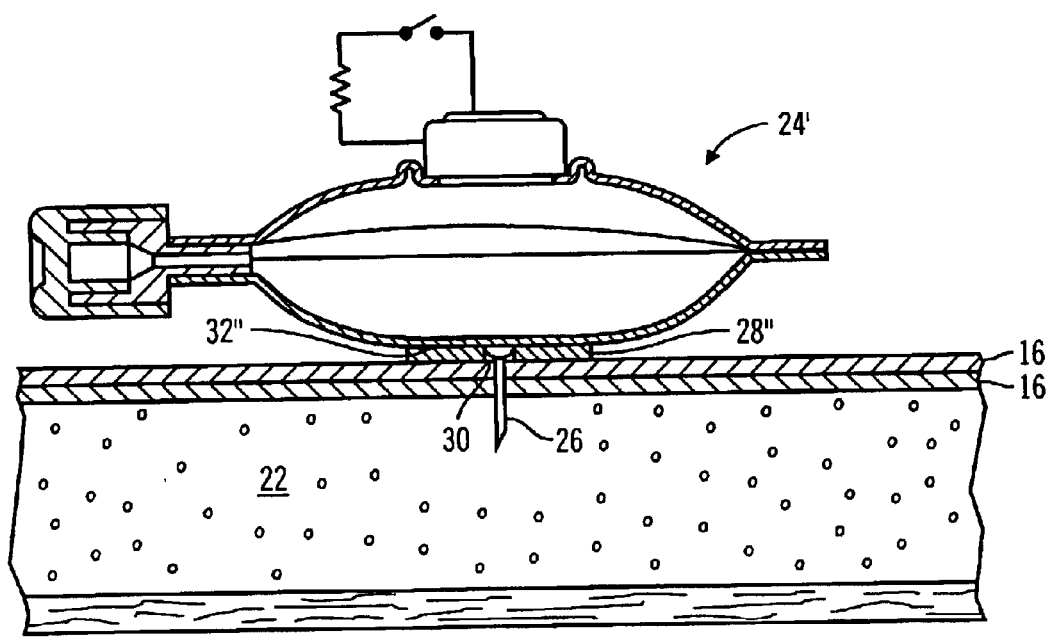
FIG. 3b is a side view of another infusion pump attached to a body tissue, showing a cross-sectional view of a delivery element penetrating the body tissue.

In operation, the fluid flows from the infusion pump 10, through the flexible tube 12, and into the delivery device, such as the infusion set 14 or the like, that is adhered to the individual's skin 16. As shown in FIG. 2a, the delivery element, such as a cannula 18 or the like, directs the fluid from a cavity 54 inside the infusion set 14, through the individual's skin 16, and into the individual's subcutaneous tissue 22. The characteristics of cannula 18, such as the length, inner and outer diameter, end configurations, and materials may vary depending on the tissue type that the cannula is inserted into, the volume and type of fluid being infused, the configuration of the delivery device, and other parameters. In alternative embodiments, the delivery device is an infusion pump 24 adhered directly to the individual's skin 16. In a particular embodiment, shown in FIG. 3a, the infusion pump 24 has a cannula 18' as the delivery element, to deliver fluid directly from the infusion pump 24 through the individual's skin 16 to the subcutaneous tissue 22. FIG. 3b shows another particular embodiment illustrating infusion pump 24' with a needle 26 for the delivery element. The infusion pump 24 may be of the type described in U.S. Pat. Nos. 4,902,278; 5,785,688; 5,814,020; 5,848,991; and 5,858,001; or other small disposable pumps for delivery of fluid through a delivery element to an individual's body. In particular embodiments, other fluid delivery elements are used, such as capillaries, conduits, needles, lumens, or the like.

In further alternative embodiments, the delivery device may be a pen injector (not shown) adapted to receive the reservoir, and may be of the type available from, but not limited to, BD Consumer Healthcare, Disetronic Medical Systems, and Eli Lilly and Company. The pen injector is held adjacent to the individual's skin during delivery of fluid into the individual's body, and then removed until the next desired delivery of fluid into the individual's body. The pen injector delivers fluid from the reservoir via a delivery element, such as a needle, through the infusion set adhered directly to the individual's skin, and into the individual's subcutaneous tissue. Alternatively, the infusion set may be omitted, and the pen injector may have a delivery element, such as a needle, to deliver fluid directly from the pen injector, through the individual's skin, and into the individual's body.

Figure 2B:
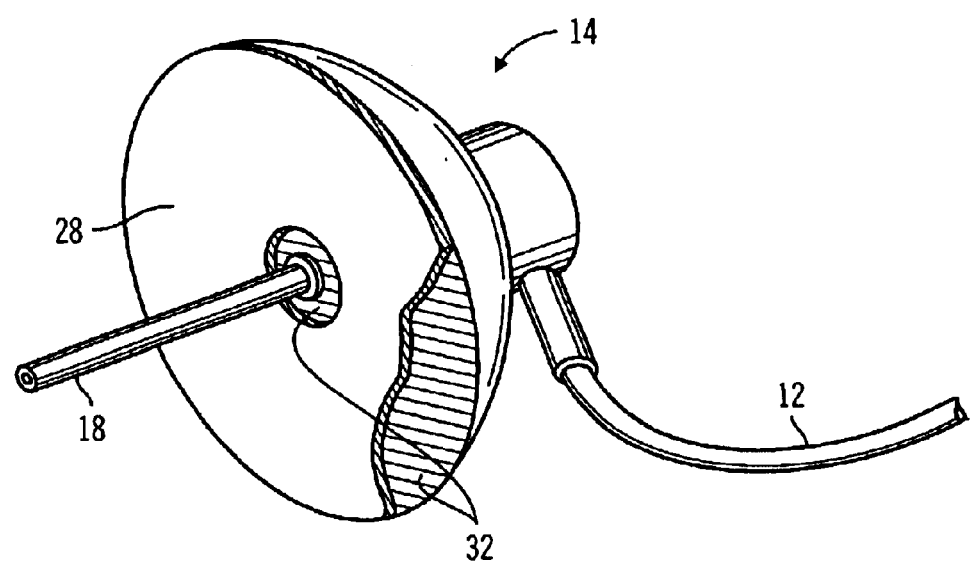
FIG. 2b is a perspective bottom view of the infusion set of FIG. 2a with a pad partially cut away.

The most common cause of leaking fluid near the infusion site 30 is due to the delivery element inadvertently slipping out of an individual's body. This generally occurs if the delivery device (an infusion set 14 or an infusion pump 24) connected to the delivery element, lifts away from the individual's skin 16. Consequently, in preferred embodiments, the delivery device includes one or more pads 28 to attach the delivery device to the individual's skin. The pads 28 include an adhesive, and the pad may be made of an adhesive, foam, glue, tape, a substrate coated with adhesive, or the like. The pads 28 are generally arranged around the infusion site 30 and serve to hold the delivery device on the individual's skin 16. One of the one or more pads 28 may be located on a delivery device base 32. Pads 28 are various sizes and shapes to accommodate the different footprints that different delivery devices have on the individual's skin 16. A pad 28 for an infusion set 14 is shown in FIGS. 2a and 2b. Pads 28' and 28", shown in FIGS. 3a and 3b respectively, are attached to the delivery device bases 32' and 32" respectively for particular embodiments of infusion pumps 24 and 24' respectively. In other embodiments, the delivery device is held to the individual's skin 16 with a tape 34. In still other embodiments, both the adhesive of the pad 28 and tape 34 are used to secure the delivery device to the individual's skin 16.

There may be other causes of leaking fluid near the infusion site 30. For example, the cannula 18 may separate from the delivery device or an inadequately sealed delivery device could leak fluid. In these cases, fluid leaking near the infusion site 30 may be trapped by the surrounding pads 28 and collect between the delivery device and the individual's skin 16. Consequently, the fluid is substantially not infused into the individual's body.

In preferred embodiments, the infused fluid is insulin. However, many other fluids may be administered through infusion, such as, but not limited to, HIV drugs, drugs to treat pulmonary hypertension, iron chelation drugs, pain medications, anti-cancer treatments, vitamins, hormones, or the like.

Figure 4:
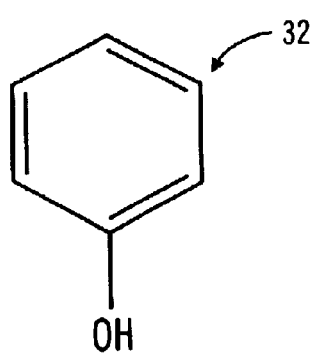
FIG. 4 is a diagram of a phenol molecule.
Figure 5:
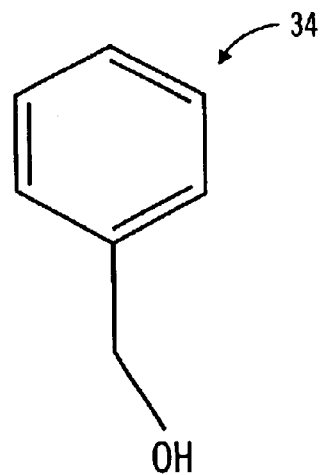
FIG. 5 is a diagram of a benzyl alcohol molecule.

Most fluids designed for parenteral administration (and/or infusion) contain a preservative. The most commonly used preservatives are based either on a phenol system 32 or a benzyl alcohol system 34. Examples of these systems are shown in FIGS. 4 and 5 respectively. Thus, one approach to detecting a leak is to trigger a chemical reaction that is observable by an individual when any of these preservatives are present in a fluid leaked near the infusion site 30.

Figure 6:
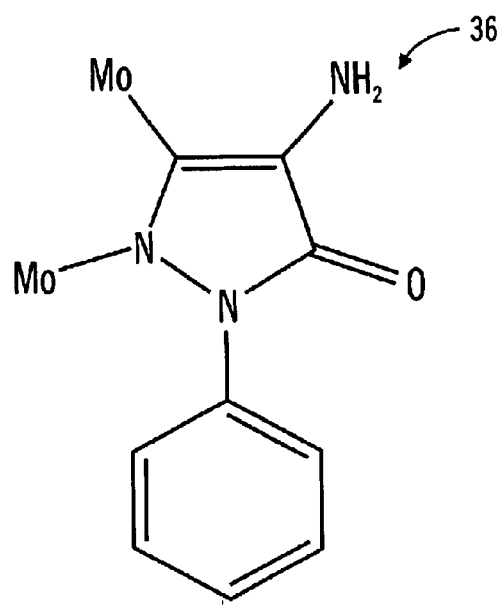
FIG. 6 is a diagram of a 4-amino-antipyrine molecule.
Figure 7:
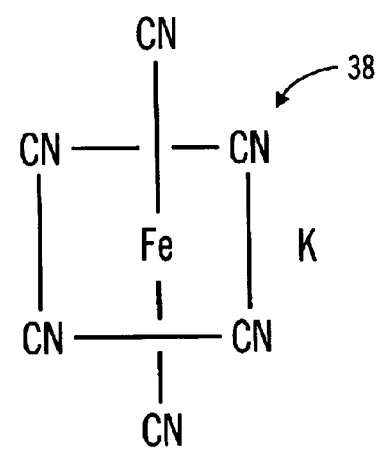
FIG. 7 is a diagram of a potassium ferricyanide ($K_3Fe(CN)_6$) molecule.

In preferred embodiments, a clear gel containing 4-amino-antipyrine 36, shown in FIG. 6, and potassium ferricyanide 38 ($K_3 Fe(CN)_6$), shown in FIG. 7, is deposited on the delivery device base 32, within the pad 28, or with an adhesive. In particular embodiments, the delivery device is a clear plastic infusion set 14 with a delivery device base 32 as shown in FIGS. 2a and 2b. In other embodiments, such as the one shown in FIG. 3a for example, the delivery device is an infusion pump 24 with clear plastic parts incorporated in the infusion pump (not shown), as necessary, for the individual to see through the infusion pump 24 and observe the gel near the infusion site 30. In alternative embodiments, the delivery device may include other clear (optically transparent) materials, such as glass, creams, crystal, laminates, or the like for the individual to see through the delivery device and observe the gel near the infusion site 30.

In other alternative embodiments, the chemicals are deposited on a pad 28 made of hydrogel, cloth, fibrous material, porous material, or other materials that wick away fluid, so that the leaking fluid from the infusion site 30 is drawn to the edges of the pad 28. Then the color change from the reaction can be seen around the edges of the delivery device. The pad 28 may extend beyond the perimeter of the delivery device so that the edges of the pad 28 are easily observable to the user. In this embodiment, portions of the delivery device or the entire delivery device may be opaque since the color change does not have to be observed through the device.

Figure 8:
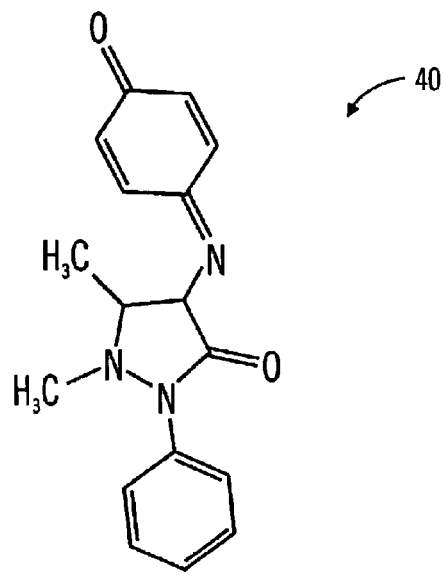
FIG. 8 is a diagram of a bright blue chemical complex.

When a leak occurs, the preservative in the parenteral fluid reacts with the 4-amino-antipyrine 36 and potassium ferricyanide 38 in the gel. The resulting product is a bright blue colored complex 40. Thus, the chemicals, seen through the delivery device or around the edges of the device, change from clear to bright blue, serving as a visual indicator to the individual that a leak has occurred. A drawing of the structure of the resulting bright blue colored complex 40 is shown in FIG. 8. The time required to detect the leak is typically one to two hours. However, the time required for detection may be short as 5 minutes or as long as 8 hours due to the concentrations of the reactants, 4-amino-antipyrine 36 and potassium ferricyanide 38, the concentration of the preservative in the fluid, the leak rate of the fluid, the rate at which the leaking fluid spreads and comes in contact with the reactants, the method used to deposit the chemicals near the infusion site 30, the temperature near the infusion site 30, and the presence of contaminants such as body fluids. In alternative embodiments, the clear gel may be some other color, such as white, cream, off white, or the like, or a contrasting color to make the color change noticeable. In other embodiments, the colored product is a different color, such as red, yellow, orange, pink, green, purple, or the like.

In alternative embodiments, an enzymatic system is used to amplify the chemical color change signal. An enzyme, such as horse radish peroxidase (HRP), is added to the gel containing 4-aminoantipyrine 36 and potassium ferricyanide 38. When a leak occurs, water in the leaking fluid dissolves the HRP. The HRP then acts as a catalyst to, in essence, create an enzymatic amplification of the signal. Again, a deep blue colored complex 40 is formed due to the phenol 32 or benzyl alcohol 34 preservatives in the fluid reacting with 4-aminoantipyrine 36 and potassium ferricyanide 38. The advantage of the HRP system is that only very small amounts of the leaked fluid need to be present to be detected. For example, with HRP present in the gel, a fluid leaking at a rate of only 8 microliters per hour can be detected in approximately 15 to 20 minutes, whereas without HRP, the same leak might take 1 to 2 hours to be detectable. In alternative embodiments, the time required to detect a leak can range from less than 20 seconds to over 4 hours depending on the concentration of HRP present in the gel, the concentration of the reactants 4-aminoantipyrine 36 and potassium ferricyanide 38, the method used to deposit the chemicals near the infusion site 30, the rate that the leaking fluid spreads and comes in contact with the reactants, the temperature near the infusion site 30, and the concentration of contaminates, such as body fluids, near the infusion site 30.

In further alternative embodiments, the 4-aminoantipyrine 36 and potassium ferricyanide 38 are encapsulated in micro-spheres and blended into the adhesive used to hold the delivery device to the individual's skin 16. In particular embodiments, the micro-spheres dissolve in the presence of an ingredient contained in the infused fluid, such as water, alcohol, or the like, which then sets the reactants free to react with the preservative in the fluid as described above. Additional embodiments include HRP encapsulated in micro-spheres along with 4-aminoantipyrine 36 and potassium ferricyanide 38. In other embodiments, different methods are employed to position the 4-aminoantipyrine 36, potassium ferricyanide 38 and perhaps HRP near the infusion site 30. These methods include mixing them directly into an adhesive, applying them with starch granules, depositing them in pockets formed in a delivery device base 32 and/or pad(s) 28, encapsulating them and mixing them with a gel, embedding them into the delivery device base 32, spreading them on the individual's skin 16, or the like. Still further embodiments apply the 4-aminoantipyrine 36 and potassium ferricyanide 38, perhaps along with HRP, to the adhesive tape 34 applied to the delivery device as an overdressing and/or an underdressing. For instance, a clear adhesive tape 34 prepared with the reactants and/or catalyst can be applied around a delivery device that is attached to the individual's skin 16. In another example, the adhesive tape 34 with reactants is placed on the individual's skin 16 under the delivery device. In both instances, when fluid leaks near the infusion site 30, the bright blue colored complex 40, product of the reaction, is visible through the adhesive tape 34.

In other embodiments, where the fluid to be delivered into an individual's body includes a protein, such as an insulin formulation, other reactants may be located near the infusion site 30 to produce a color change that signifies a leak. In particular embodiments, either ninhydrin or Coomassie Brilliant Blue reacts with the protein in the fluid resulting in a brightly colored product. A potential drawback to both of these reactants is that it will irreversibly stain the individual's skin 16 until the individual's skin 16 is exfoliated. Thus, other non-staining compounds might be used.

While the chemical reactions above are described with reference to detecting when fluid is leaking near the infusion site 30, it should be appreciated that these chemical reactions may also be used to detect when fluid is leaking from or near fluid containing elements within the fluid delivery system. For example, a common cause of leaking fluid within the fluid delivery system is due to a damaged reservoir or a leaking interface at the connection between the reservoir and the flexible tube.

In preferred embodiments, shown in FIGS. 11 and 12, one or more of the chemicals described above, which produce a color change when fluid is leaking from the reservoir 11 or 11', are deposited on an exterior surface of the reservoir 11 or 11'. Additionally, one or more of the catalysts described above, which amplify the color change from the chemical reaction, may also be deposited on the exterior surface of the reservoir 11 or 11'. Further, these reactants may be deposited on one of the wicking materials described above, which may then be deposited on the exterior surface of the reservoir 11 or 11', in order to draw the leaking fluid along a larger surface of the reservoir 11 or 11' and make the color change from the chemical reaction more easily observable to the user. For example, the wicking material may draw the leaking fluid toward the portion of the reservoir 11 or 11' that is visible through the window 17 (not shown in FIG. 12) in the pump housing 44 or 44', or toward the connector 19 or 19' and the tube 12 or 12' that are visible from the exterior of the pump housing 44 or 44', so that the color change from the chemical reaction is visible to the user while the reservoir 11 or 11' is seated within the pump housing 44 or 44'. When fluid is leaking from the reservoir 11 or 11', these reactants on the exterior surface of the reservoir 11 or 11' produce a color change that is easily observable by the user.

In one embodiment, the reactants may be deposited on the entire exterior surface of the reservoir 11 or 11', including for example, the connector 19 or 19', the neck, and the barrel 23 or 23'. The reactants are preferably clear or transparent so that the user can still view the fluid contained within the reservoir 11 or 11'. In alternative embodiments, the reactants may be deposited only on or near the interface between the reservoir 11 or 11' and the connector 19 or 19', such as on the neck of the reservoir 11 or 11' and/or an upper portion of the barrel 23 or 23' of the reservoir 11 or 11', as this interface is a common source of leaking fluid within the fluid delivery system. In further alternative embodiments, the reactants may be deposited on portions of the interior surface of the connector 19 or 19' that are not wetted by the fluid when the fluid flows along the normal fluid path, but that may become wet when the fluid leaks outside the normal fluid path.

The reactants may be deposited on the exterior (and interior, if desired) surface of the components, such as the reservoir 11 or 11', the tube 12 or 12', and/or the connector 19 or 19', by different methods. In one embodiment, the reactants are sprayed directly onto the surface of one or more of the components. In alternative embodiments, the reactants may be deposited onto the surface of one or more of the components by other methods described above, such as applying a gel containing the reactants, and the like. In further alternative embodiments, a label may be prepared with the reactants on one or both sides of the label, and the label may be applied onto the reservoir 11 or 11', the tube 12 or 12', and/or the connector 19 or 19'. For example, if the reservoir 11 or 11' is made of a generally durable material (e.g., plastic), a label coated with the reactants on the exterior of the label may be applied onto the reservoir 11 or 11'. Alternatively, if the reservoir 11 or 11' is made of a breakable material (e.g., glass), a label coated with the reactants on both the interior and exterior of the label may be applied onto the reservoir 11 or 11'. In this manner, leaking fluid due to a broken reservoir 11 or 11' may be detected by the reactants on the interior of the label, and other leaking fluid, such as from a defective interface at the connector 19 or 19' between the reservoir 11 or 11' and the tube 12 or 12', may be detected by the reactants on the exterior of the label. The label may also be made from one of the wicking materials described above in order to draw the leaking fluid along a larger surface of the reservoir 11 or 11'.

In other embodiments, rather than depositing the reactants onto the exterior (and interior, if desired) surface of the reservoir 11 or 11', the reactants may be deposited onto portions of the pump housing 44 or 44', such as the reservoir compartment 13 or 13', the door 15, the window 17 (not shown in FIG. 12), or the like. In particular embodiments, a disposable label or sleeve may be coated with the reactants and then adhered to a portion of the pump housing 44 or 44'. When fluid is leaking from the reservoir 11 or 11', the reactants on the label produce a color change that is easily observable by the user. Once fluid has leaked onto the label, the user may remove and replace the used, discolored label with a new label. In alternative embodiments, the reactants may be deposited directly onto one or more portions of the pump housing 44 or 44'. When fluid is leaking from the reservoir 11 or 11', the reactants on the pump housing 44 or 44' produce a color change that is easily observable by the user. Once fluid has leaked onto the reactants applied on a particular portion of the pump housing 44 or 44', the user may wipe off and reapply the reactants on that portion and/or other portions of the pump housing 44 or 44'.

While the chemical reactions described above are effective at displaying a visual signal (a color change) when fluid is leaking, the individual must visually inspect around the location of the leak, such as near the infusion site 30 or the reservoir 11, to see the visual signal. Thus, alternative methods of leak detection utilize an audible or tactile notification of a leak in addition to, or instead of, a visual only signal.

In particular embodiments, optical or electrical detection methods provide a signal to electronics contained within the infusion pump housing 44. When a leak is detected, the electronics activate an alarm. Specific embodiments include an audible alarm that the individual can hear when a leak is detected. Alternative embodiments have other alarm mechanisms such as a vibrator, flashing lights or LEDs, an LCD backlight, an LCD message displaying the cause for alarm, a small scintillating electric shock to the individual, a heating element, or the like. In other alternative embodiments, the alarm generates at least one notification signal, such as by telemetry, radio frequency, optical, infrared, ultrasonic, laser, telephone, pager, or the like. Infusion pump communication apparatuses and methods are disclosed in U.S. Patent Application Serial No. 60/096,994, filed Aug. 18, 1998 and entitled "Infusion Device With Remote Programming, Carbohydrate Calculator And/Or Vibration Alarm Capabilities", which is herein incorporated by reference. In particular embodiments, an alarm notification is stored in a memory device, such as an on-board memory chip, a computer memory, a palm pilot, computer disks, compact disks, a telephone message, a pager, or the like. In other embodiments, the alarm notifies a person other than the individual using the infusion pump (10 or 24), i.e. a doctor, a nurse, a parent, a spouse, a friend, a relative, a work mate, or the like.

Figure 9:
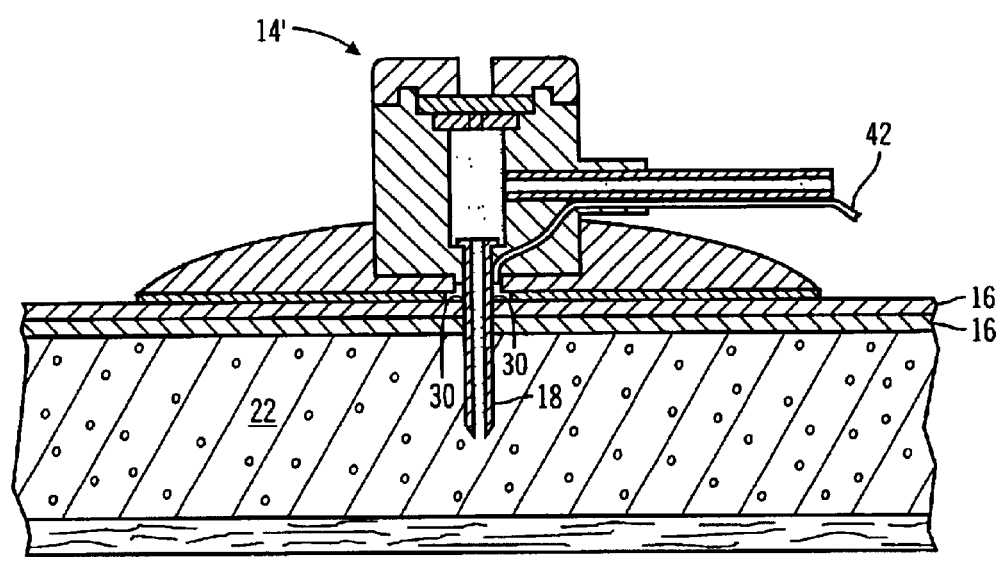
FIG. 9 is a cross-sectional side view of the infusion set of FIG. 2a, with a fiber optic cable.

Some embodiments of the current invention use an electro-optical detection system in combination with any of the chemical reactions that result in a colored chemical product like those previously described. An optical receiver receives light from near the infusion site 30. When chemical reactants produce a colored product, the optical receiver detects a change in the light indicating a fluid has leaked. The optical receiver provides an output signal to the electronics. In particular embodiments, a miniature optical transmitter and receiver are located near the infusion site 30. The exterior surface of either the transmitter, or the receiver, or both, are coated with reactants that will produce a colored complex 40 in the presence of the leaking fluid. When a leak triggers the color change, the optical signal between the optical transmitter and optical receiver is altered. The optical signal is carried to the electronics by a fiber optical cable 42, or is converted to an electrical signal and carried to the electronics by electrical wire, or the like. FIG. 9 illustrates a fiber optic cable 42 that carries a light signal from the infusion site 30 through the infusion set 14'. Chemically activated color changes are detected by the optical receiver through the fiber optic cable 42. In alternative embodiments, more than one fiber optic cable 42 may be used to carry light from more than one location near the infusion site 30 to the optical receiver. In another embodiment, the optical receiver and an optical transmitter are both located inside the infusion pump housing 44. A first fiber optic cable runs from the optical transmitter to a point near the infusion site 30, and a second fiber optic cable runs from the optical receiver to a point near the infusion site 30. The ends of the fiber optic cables near the infusion site 30 are positioned with respect to each other so that light emitted by the optical transmitter is detected by the optical receiver. A gap exists between the ends of the fiber optic cables near the infusion site 30. Gel, or adhesive, or another carrier media containing the reactants, is placed in the gap between the ends of the fiber optic cables. When a leaking fluid triggers a reaction producing a chemical color change, a change in the light signal is detected by the optical receiver.

Still other embodiments take advantage of the light conducting characteristics of the flexible tube 12 when it is filled with the fluid. An optical receiver, located in the infusion pump housing 44, is positioned, with respect to a first end of the flexible tube 12, to receive light carried through the flexible tube 12 from an infusion set. In particular embodiments, a second end of the flexible tube 12 is positioned with respect to the cannula 18 of the infusion set, such that light entering an exposed cannula 18 travels through the flexible tube 12 to the optical receiver. While the cannula 18 is in the individual's body, the optical receiver detects virtually no light since very little light passes through the body tissue surrounding the cannula 18. When the cannula 18 is pulled out, light enters the cannula 18 and is detected by the optical receiver. The optical receiver responds particularly to light wavelengths that are substantially absorbed or blocked by tissues near the surface of the body. In other embodiments, the second end of the flexible tube 12 is positioned to receive light from an area near the infusion site 30. When a leak causes a chemical reaction resulting in a color change near the infusion site 30, the light traveling through the flexible tube changes color and the optical receiver detects a change in light indicating that a leak has occurred.

In embodiments that do not use a flexible tube 12 between the delivery device and the infusion pump 10, for example, when the infusion pump is attached directly to the individual's skin 16 near the infusion site 30, the optical receiver is located within the infusion pump housing and is positioned with respect to the cannula 18 (or needle 26) such that light coming from the cannula 18 (or needle) is detected by the optical receiver. If sufficient light is detected by the optical receiver, it is an indication that the cannula (or needle 26) is not in the individual's body and a leak has occurred.

In alternative embodiments, the optical and electro-optical detection systems, which have been described above for detecting fluid leaking near the infusion site 30, may also be used to detect when fluid is leaking near other locations within the fluid delivery system. For example, referring to FIGS. 11 and 12, the optical and electro-optical detection systems described above may be used to detect when fluid is leaking from or near fluid containing elements within the fluid delivery system, such as on or near the reservoir 11 or 11', along the flexible tube 12 or 12' between the infusion pump 10 or 10' and the delivery device, or the like. The optical receiver and/or transmitter may be placed near a fluid containing element coated with the chemical reactants for producing a color change described above, such as the reservoir 11 or 11' (including on or near the connector 19 or 19'), the flexible tube 12 or 12', or the like. Alternatively, the optical receiver and/or transmitter may be placed near a portion of the pump housing coated with the chemical reactants, such as the reservoir compartment 13 or 13', the door 15, the window 17 (not shown in FIG. 12), or the like. In particular embodiments, the fiber optic cable may carry a light signal to the optical receiver from the location of a fluid leak, such as on or near the reservoir 11 or 11', along the flexible tube 12 or 12', or the like. In other embodiments, the window 17 (not shown in FIG. 12) or other portions of the pump housing 44 or 44' that are transparent may provide light to the optical receiver from near the fluid containing element, such as the reservoir 11 or 11' (including the connector 19 or 19'), or the like. In further alternative embodiments, the optical receiver and/or transmitter may be coated with the chemical reactants, and then placed near or in contact with a fluid containing element, such as the reservoir 11 or 11' (including on or near the connector 19 or 19'), the flexible tube 12 or 12', or the like.

Other leak detection methods are based on electrical measurements. An infusion pump battery is an available source for the electrical power required to operate an electrically based detection apparatus. Electronics contained within the infusion pump housing 44 evaluate the signals from the electrically based detection apparatus. In preferred embodiments, conductive leads such as, wires, conductors, traces, or the like, are enclosed within the wall of the flexible tube 12 that carries the fluid from the infusion pump 10 to an infusion set 14. In particular embodiments, the conductive leads run through the flexible tube walls in a helical path. In other embodiments the conductive leads run straight down the flexible tube 12. Alternatively, in other embodiments, the conductive leads are external to the flexible tube 12. Additionally, embodiments that include an infusion pump 24 adhered to the individual's skin 16 may have conductive leads contained within the infusion pump housing 44 if needed. Further alternative embodiments may include external conductive leads that are printed, silk screened, stamped, ink jetted, adhered, or the like onto the flexible tube 12.

Figure 10A:
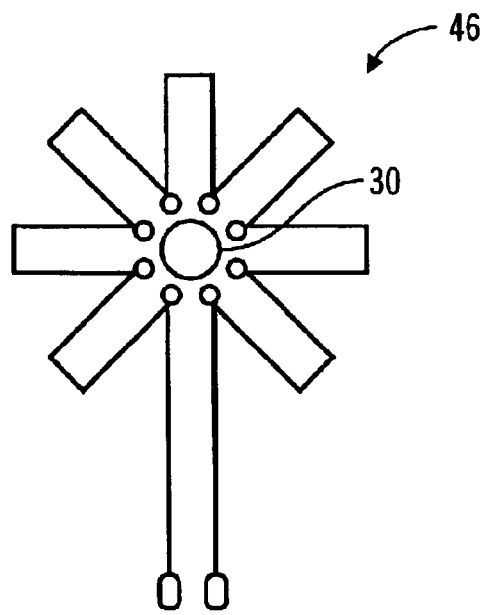
FIG. 10a is a top view diagram of an uninterrupted rosette substantially surrounding an infusion site.

In preferred embodiments, a rosette, which is a pattern of one or more conducting elements, is embedded in the delivery device base, or applied to the surface of the delivery device base, to substantially surround the infusion site 30. Conducting elements may be wires, sputtered carbon, plastics doped with conductive fillers, epoxies doped with conductive fillers, or the like. Particular embodiments employ an active electronic signal to detect changes in impedance across the rosette. For instance, a voltage is supplied across the rosette by running conductive leads from the pump battery to different points on the rosette, such as opposite or adjacent end points. Then the impedance is measured across the rosette. When fluid leaks onto the rosette, the impedance changes and the electronics measure the change in impedance to detect a leak. In preferred embodiments, an uninterrupted rosette 46 is used, such as an example shown in FIG. 10a; when a fluid leaks near the infusion site 30, it shorts out portions of the rosette 46 providing additional or shorter conductive paths across portions of the rosette 46, and the total impedance across the rosette 46 decreases. The reduction in impedance across the rosette 46 is detected by the electronics which indicates a fluid leak. Many other uninterrupted rosette patterns will work as long as fluid leaking near the infusion site 30 will short out a sufficient portion of the rosette for a measurable change in impedance to be detectable. Uninterrupted rosettes have a continuous conductive path so that the voltage drop across the rosette is measurable, and is not zero. Thus, a test voltage may be used to confirm that there are no disconnects or opens in the circuit leading from the electronics to the rosette and back. In preferred embodiments, the impedance of the fluid to be detected, and the impedance of the conductive leads leading from the electronics to the rosette are low compared to the impedance across the rosette. Thus, the high impedance of the rosette decreases rapidly as relatively highly conductive fluid spreads across the rosette. In alternative embodiments, the impedance of the fluid and or the leads is not low compared to the impedance of the rosette, and therefore the electronics are tuned to detect small shifts in the change of the impedance across the rosette.

Figure 10B:
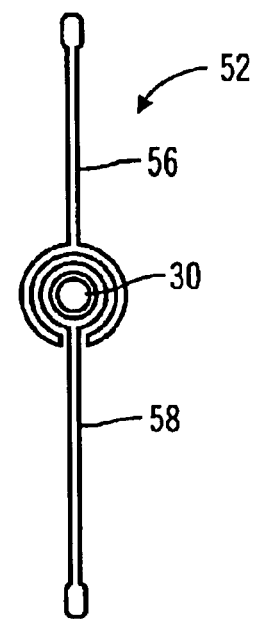
FIG. 10b is a top view diagram of a discontinuous rosette substantially surrounding an infusion site.
Figure 10C:
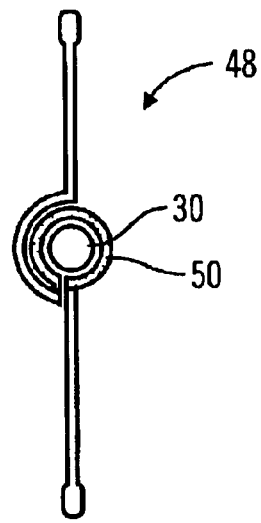
FIG. 10c is a top view diagram of an uninterrupted rosette with a dissolvable portion substantially surrounding an infusion site.

In other embodiments, portions of the rosette are designed to dissolve away in the presence of the fluid being infused. An example of a particular embodiment of an uninterrupted rosette 48 with a dissolvable portion 50 near the infusion site 30 is shown in FIG. 10c. When a leak occurs, at least a part of the dissolvable portion 50 of the rosette 48 dissolves, and the impedance across the rosette 48 increases. In fact, if enough of the rosette 48 dissolves, the rosette 48 may become an open circuit. This increased impedance is detected by the infusion pump electronics. Many different continuous rosette patterns may be used so long as the dissolvable portion of the rosette substantially surrounds the infusion site 30. This embodiment functions even if the fluid is not conductive.

In alternative embodiments, the rosette is discontinuous. The conductive path is interrupted and fluid leaked near the infusion site 30 is required to close the open circuit. Although many designs of discontinuous rosettes may be used, one embodiment is shown in FIG. 10b. The normal voltage reading across the discontinuous rosette 52 is zero. Fluid leaked near the infusion site 30 shorts portions of the rosette 52 and closes the circuit. The conductive leads, the rosette 52, and the fluid near the infusion site 30 must have sufficiently high conductivity compared to an open circuit for the fluid to be detected. In other embodiments, a change in capacitance is measured to detect the presence of a fluid.

In another embodiment, compounds are added into the adhesive so that the conductive properties of the adhesive change in the presence of the infused fluid. However, it is preferred that the presence of salt, water or sweat alone does not change impedance of the adhesive, or if the impedance does change due to salt, water or sweat, that it changes in a predetermined or predictable manner. A rosette, on the delivery device base, substantially surrounds the infusion site 30, and is in direct contact with the adhesive, but the rosette is insulated from the individual's skin 16 by the adhesive. Therefore, the rosette does not undergo a change in impedance due to natural body fluids on the surface of the individual's skin 16. However, when a fluid leak occurs, the impedance of the adhesive changes, and therefore, the impedance measured across the rosette changes, which is then detected by the electronics.

In alternative embodiments, the rosette may be in contact with a material that wicks fluid away from near the infusion site 30 and spreads the fluid quickly across the rosette for an accelerated response. In further embodiments, a wicking material may be used with the chemical reactions described above, to accelerate the reaction or make the resulting product of the reaction more visible.

In other embodiments, electrical power is not supplied to the rosette. Instead, leaking fluid reacts with one or more chemical compounds in contact with a rosette near the infusion site 30. The electrochemical reaction generates an electrical charge, and the voltage measured across a discontinuous rosette increases from zero to a detectable voltage level indicating that the fluid has leaked. In particular embodiments, two unconnected electrodes 56 and 58, of rosette 52 shown in FIG. 10b, are made of different metals and coated with different chemicals. The electrodes 56 and 58 are separated from the skin by a material such as a hydrogel or other material that is dry before a leak occurs, yet after a leak the wetted hydrogel or other material conducts electricity. Either of the electrodes, 56 for example, is made of platinum and is coated with HRP and 4-aminoantipyrine 36. The other electrode, 58 for example, is made of silver that is chloridized. When the electrodes 56 and 58 are dry, there is no voltage across the electrodes 56 and 58. Once a leak occurs, the phenol 32 or other preservative within the leaking fluid begins to react with the HRP and 4-aminoantipyrine 36. The voltage across the electrodes 56 and 58 will be about 650 mV or less. In one embodiment, the voltage is applied across an LED (not shown) included as part of the infusion set 14, causing the LED to flash when a leak is detected. In alternative embodiments, the resulting voltage generated across the electrodes 56 and 58 is applied to other notification devices included as part of the infusion set 14 such as a piezo electric sound emanating device, another sound emanating device, a piezo electric vibration device, another vibration device, a LED that lights up or changes color when the voltage is supplied, a RF transmitting device that signals the infusion pump 10, or the like. In other alternative embodiments, the voltage across the electrodes 56 and 58 is carried by a wire to the infusion pump 10 and the infusion pump 10 triggers an alarm. In still other embodiments, the voltage is applied to the individual's skin 16 to notify the individual with a minor electric shock. In other particular embodiments, other concentrations or other reactants may be used to generate a greater or lesser voltage differential across the electrodes 56 and 58. In other embodiments, electrode 58 is made of platinum and is coated with HRP and 4-aminoantipyrine 36, and the other electrode 56 is made of silver that is chloridized. In additional embodiments, other discontinuous rosettes are used.

In further embodiments, a change in impedance is detected if a delivery device, such as an infusion set 14 or an infusion pump 24, lifts off of the individual's skin 16 and the delivery element, such as a cannula 18 or a needle 26, becomes dislodged from the subcutaneous tissue 22. A change in impedance indicates that the delivery element is no longer in the individual's body, and therefore the fluid is leaking. In particular embodiments, a pair of electrodes are mounted on the delivery device base to measure impedance across the individual's skin 16. When one or both electrodes lose contact with the individual's skin 16, the increased impedance between the electrodes is sensed by the infusion pump electronics indicating a fluid leak. Alternatively, a change in capacitance between the electrodes may be measured to detect when the delivery device lifts off of the individual's skin 16. The relative capacitance increases when one or more electrodes lose touch with the individual's skin 16.

Other embodiments use electrodes located on an exterior of the cannula to detect whether the delivery element is inserted in the individual's body. Body fluid in the subcutaneous tissue 22 is substantially more conductive than infused fluids. When a cannula is pulled from the body, the measured impedance across the electrodes on the cannula increases, indicating that a leak is detected. Particular embodiments include a non-removable needle centered inside a cannula as one electrode and a metal sheath on the external surface of the cannula as the other electrode. In an alternative embodiments, the electrodes are conductive strips on the external surface of the cannula. Other embodiments include a first electrode attached to the delivery element, such as a cannula or a needle, and a second electrode touching the surface of the individual's skin 16, such as on the delivery device base attached to the individual's skin 16. This method is easier to use if the delivery element inserted in the individual's body is conductive, such as a steel needle, a cannula with a conductive coating, a cannula with conductors on the exterior surface, or the like. Again, impedance increases when the delivery element is pulled out of the individual's body. Alternatively, capacitance is measured instead of impedance, since capacitance increases when the delivery element is pulled out of the individual's body.

In yet other embodiments, the detection systems based on electrical measurements, which have been described above with reference to detecting when fluid is leaking near the infusion site 30, may also be used to detect when fluid is leaking near other locations within the fluid delivery system. For example, referring to FIGS. 11 and 12, the electrical detection systems described above may be used to detect when fluid is leaking from or near fluid containing elements within the fluid delivery system, such as on or near the reservoir 11 or 11' containing the fluid to be delivered into the individual's body, along the flexible tube 12 or 12' between the infusion pump 10 or 10' and the delivery device, or the like. The rosette may be placed on or near the reservoir 11 or 11' (such as on or near the connector 19 or 19'), the flexible tube 12 or 12' between the infusion pump 10 or 10' and the delivery device, or the like.

In alternative embodiments, the leaking fluid triggers an exothermic chemical reaction. The individual feels their skin near the infusion site 30 become warm when a leak occurs. Visual inspection of the infusion site 30 is replaced by a tactile temperature change. In other embodiments, both the color change method and an exothermic reaction are used.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In a fluid delivery system for delivering a fluid into an individual's body, a leak detection system to detect the presence of the fluid that has leaked outside a normal fluid path of the fluid delivery system, the leak detection system comprising:

a fluid containing element adapted to be filled with the fluid to be delivered into the individual's body and placed in a device for delivering the fluid into the individual's body;

a delivery element configured to penetrate the individual's body and establish fluid communication between the fluid containing element and the individual's body so that the fluid can travel along the normal fluid path from the fluid containing element through the delivery element into the individual's body; and at least one chemical, positioned near the fluid containing element, that reacts with at least one component within the fluid when the fluid is present near an exterior surface of the fluid containing element.

2. A leak detection system according to claim 1, wherein a product of a chemical reaction, between the at least one chemical positioned near the fluid containing element and the at least one component within the fluid, is a colored complex.

3. A leak detection system according to claim 1, wherein the at least one chemical positioned near the fluid containing element contains at least 4-amino-antipyrine and potassium ferricyanide.

4. A leak detection system according to claim 1, wherein the at least one chemical positioned near the fluid containing element contains at least 4-amino-antipyrine and potassium ferricyanide and horse radish peroxidase (HRP).

5. A leak detection system according to claim 1, wherein the at least one chemical positioned near the fluid containing element contains at least ninhydrin.

6. A leak detection system according to claim 1, wherein the at least one chemical positioned near the fluid containing element contains at least Coomassie Brilliant Blue.

7. A leak detection system according to claim 1, wherein the at least one chemical positioned fluid containing element is encapsulated in micro-spheres.

8. A leak detection system according to claim 1, wherein the at least one chemical positioned near the fluid containing element is a component of a gel.

9. A leak detection system according to claim 1, wherein the at least one chemical positioned near the fluid containing element is a component of an adhesive.

10. A leak detection system according to claim 1, wherein the at least one chemical positioned near the fluid containing element is associated with starch granules.

11. A leak detection system according to claim 1, wherein the fluid containing element is a reservoir.

12. A leak detection system according to claim 1, wherein the fluid containing element is a tube coupled between the delivery element and the device for delivering the fluid into the individual's body.

13. A leak detection system according to claim 1, wherein the at least one chemical positioned near the fluid containing element is deposited on the exterior surface of the fluid containing element.

14. A leak detection system according to claim 1, wherein the at least one chemical positioned near the fluid containing element is associated with a label applied onto the exterior surface of the fluid containing element.

15. A leak detection system according to claim 1, wherein the at least one chemical positioned near the fluid containing element is deposited on a portion of the device for delivering the fluid into the individual's body.

16. A leak detection system according to claim 1, wherein the at least one chemical positioned near the fluid containing element is associated with a label applied onto a portion of the device for delivering the fluid into the individual's body.

17. A leak detection system according to claim 1, wherein the device for delivering the fluid into the individual's body is an infusion pump.

18. A leak detection system according to claim 1, wherein the device for delivering the fluid into the individual's body is a pen injector.

19. In a fluid delivery system for delivering a fluid into an individual's body, a leak detection system to detect the presence of the fluid that has leaked outside a normal fluid path of the fluid delivery system, the leak detection system comprising:
- a fluid containing element adapted to be filled with the fluid to be delivered into the individual's body and placed in a device for delivering the fluid into the individual's body;
- a delivery element configured to penetrate the individual's body and establish fluid communication between the fluid containing element and the individual's body so that the fluid can travel along the normal fluid path from the fluid containing element through the delivery element into the individual's body;
- at least one chemical positioned near the fluid containing element that reacts with at least one component within the fluid when the fluid is present near an exterior surface of the fluid containing element;
- a product of a chemical reaction between the at least one chemical positioned near the fluid containing element and the at least one component within the fluid is a colored complex;
- an optical receiver that detects a change in light when the colored complex is created by the chemical reaction and provides an output signal indicating that a leak is detected; and
- a light conducting element that guides light from a point near the fluid containing element to the optical receiver.

20. A leak detection system according to claim 19, wherein the light conducting element is at least one fiber optic cable.

21. A leak detection system according to claim 19, wherein the light conducting element is a window on the device for delivering the fluid into the individual's body.

22. A leak detection system according to claim 19, wherein the leak detection system includes an alarm system, controlled by the output signal, to notify the individual when a leak is detected.

23. A leak detection system according to claim 22, wherein the alarm system produces an audible sound when a leak is detected.

24. A leak detection system according to claim 22, wherein the alarm system activates a vibrator when a leak is detected.

25. A leak detection system according to claim 22, wherein the alarm system activates a light when a leak is detected.

26. A leak detection system according to claim 22, wherein the alarm system transmits a notification signal to another device when a leak is detected.

27. A leak detection system according to claim 22, wherein the alarm system indicates on a display when a leak is detected.

28. In a fluid delivery system for delivering a fluid into an individual's body, a leak detection system to detect the presence of the fluid that has leaked outside a normal fluid path of the fluid delivery system, the leak detection system comprising:
- a fluid containing element adapted to be filled with the fluid to be delivered into the individual's body and placed in a device for delivering the fluid into the individual's body;
- a delivery element configured to penetrate the individual's body and establish fluid communication between the fluid containing element and the individual's body so that the fluid can travel along the normal fluid path from the fluid containing element through the delivery element into the individual's body;
- a rosette positioned near the fluid containing element;
- at least one electrical component coupled to the rosette to detect a change in at least one electrical characteristic associated with the rosette when a leak occurs; and
- a battery to supply power to the at least one electrical component.

29. A leak detection system according to claim 28, wherein the rosette is a closed circuit, such that the impedance across the rosette decreases as fluid leaks near the fluid containing element.

30. A leak detection system according to claim 28, wherein the rosette is a closed circuit before a leak occurs, and at least one portion of the rosette dissolves in the presence of the fluid, such that the impedance across the rosette increases as the at least one portion of the rosette dissolves.

31. A leak detection system according to claim 28, wherein the rosette is an open circuit, such that the circuit is closed when fluid leaks near the fluid containing element.

32. A leak detection system according to claim 31, wherein one or more chemicals are positioned near the fluid containing element and wherein leaking fluid near the fluid containing element triggers an electrochemical reaction with the chemicals.

33. A leak detection system according to claim 28, wherein the at least one electrical component detects voltage across the rosette.

34. A leak detection system according to claim 28, wherein the at least one electrical component detects impedance across the rosette.

35. A leak detection system according to claim 28, wherein the at least one electrical component detects capacitance across the rosette.

36. A leak detection system according to claim 28, wherein the leak detection system includes an alarm system, coupled to the battery and the at least one electrical component, to notify the individual when a leak is detected.

37. A leak detection system according to claim 36, wherein the alarm system produces an audible sound when a leak is detected.

38. A leak detection system according to claim 36, wherein the alarm system activates a vibrator when a leak is detected.

39. A leak detection system according to claim 36, wherein the alarm system activates a light when a leak is detected.

40. A leak detection system according to claim 36, wherein the alarm system transmits a notification signal to another device when a leak is detected.

41. A leak detection system according to claim 36, wherein the alarm system indicates on a display when a leak is detected.

42. In a fluid delivery system for delivering a fluid into an individual's body, a leak detection system to detect the presence of the fluid that has leaked outside a normal fluid path of the fluid delivery system, the leak detection system comprising:

a device for delivering the fluid into the individual's body;

a fluid containing element adapted to be filled with the fluid to be delivered into the individual's body and placed in the device for delivering the fluid into the individual's body;

a delivery element configured to penetrate the individual's body and establish fluid communication between the fluid containing element and the individual's body so that the fluid can travel along the normal fluid path from the fluid containing element through the delivery element into the individual's body; and at least one chemical, positioned near the fluid containing element, that reacts with at least one component within the fluid when the fluid is present near an exterior surface of the fluid containing element; and at least one reactive element positioned near the fluid containing element and coupled to at least one of the delivery device and the fluid containing element so that when the fluid is present near an exterior surface of the fluid containing element, the at least one reactive element reacts with at least one component within the fluid.

* * * * *